US00RE38214E

(19) United States
(12) Reissued Patent
Lacey et al.

(10) Patent Number: US RE38,214 E
(45) Date of Reissued Patent: Aug. 12, 2003

(54) MICROPLATES WITH UV PERMEABLE BOTTOM WELLS

(75) Inventors: William J. Lacey, North Andover, MA (US); Gregory Mathus, Concord, MA (US); Paul M. Szlosek, Kennebunk, ME (US)

(73) Assignee: Corning Incorporated, Corning, NY (US)

(21) Appl. No.: 09/760,250

(22) Filed: Jan. 12, 2001

Related U.S. Patent Documents

Reissue of:
(64) Patent No.: 5,858,309
Issued: Jan. 12, 1999
Appl. No.: 08/621,085
Filed: Mar. 22, 1996

(51) Int. Cl.[7] ..... B01L 3/00

(52) U.S. Cl. ..... 422/102; 422/99

(58) Field of Search ..... 422/102, 99, 101, 422/104; 435/288.4, 305.1, 305.2, 288.3; 356/246, 440

(56) References Cited

U.S. PATENT DOCUMENTS

| | | | | |
|---|---|---|---|---|
| 4,302,534 | A | 11/1981 | Halmann et al. | 435/5 |
| 4,385,115 | A | 5/1983 | DeZabala et al. | 435/33 |
| 4,424,067 | A | 1/1984 | Tarasenko et al. | 95/48 |
| 4,948,442 | A | 8/1990 | Manns | 156/73.1 |
| 4,973,742 | A | 11/1990 | Ohsaka et al. | 560/184 |
| 5,319,436 | A | 6/1994 | Manns et al. | 356/246 |
| 5,487,573 | A | 1/1996 | Panek et al. | 285/332 |
| 5,487,872 | A | 1/1996 | Hafeman et al. | 422/102 |
| 5,540,978 | A | 7/1996 | Schrenk | 428/212 |
| 5,580,258 | A | 12/1996 | Wakata | 422/100 |

OTHER PUBLICATIONS

Kingsley et al., Preparation of Cultured Mammalian Cells for Transmission and Scanning Electron Microscopy Using Aclar Film, Journal of Electron Microscopy Technique, 10:77–85 (1988).

*Primary Examiner*—Alexander Markoff
(74) *Attorney, Agent, or Firm*—Thomas R. Beall; Scott S. Servilla

(57) ABSTRACT

Microplates and methods for manufacturing microplates. The microplate is designed to allow UV radiation to pass through the bottom wells of the microplate so that the microplate can be used for assaying samples by use of UV absorbance. In one embodiment, the microplate comprises at least first and second wells, each well having a UV permeable bottom. In another embodiment, the microplate comprises a frame having an upper portion and a lower portion contiguous with the upper portion and a sheet disposed between the upper portion and the lower portion and defining the bottom of at least one well of the microplate. One embodiment of the method includes steps of inserting a sheet of UV permeable material into a mold cavity that includes sections shaped to form the sidewalls of the plurality of wells, injecting molten plastic material into the mold cavity, and cooling the plastic material to form the microplate with the plastic material forming the sidewalls of each of the first and second wells and the sheet of UV permeable material forming the bottom of each of the first and second wells. Another embodiment of the method includes providing an upper plate defining sidewalls of at least one well, adhering an intermediate layer to the upper plate and adhering a sheet of UV permeable material to the intermediate layer. A further embodiment of the method includes inserting a sheet of material having at least one hole into a mold cavity, injecting a molten plastic material into the mold cavity and cooling the plastic material to form a microplate.

27 Claims, 15 Drawing Sheets

MICROPLATES WITH UV PERMEABLE BOTTOM WELLS

Matter enclosed in heavy brackets [ ] appears in the original patent but forms no part of this reissue specification; matter printed in italics indicates the additions made by reissue.

FIELD OF THE INVENTION

The present invention relates generally to microplates for assaying samples, and more specifically to microplates that have UV permeable bottom wells and methods of making such microplates.

BACKGROUND OF THE INVENTION

The recent growth in many areas of biotechnology has increased the demand to perform a variety of studies, commonly referred to as assays, of biochemical systems. These assays include, for example, biochemical reaction kinetics, DNA melting point determinations, DNA spectral shifts, DNA and protein concentration measurements, excitation/emission of fluorescent probes, enzyme activities, enzyme-cofactor assays, homogeneous assays, drug metabolite assays, drug concentration assays, dispensing confirmation, volume confirmation, solvent concentration confirmation and solvation confirmation. Since most components of biochemical systems absorb radiation in the ultraviolet (UV) region of the electromagnetic spectrum (200 nm to 400 nm), UV absorption spectroscopy may be used to study these systems. In addition, UV absorption spectroscopy offers the advantages of relatively high precision and accuracy.

Assays of biochemical systems are carried out on a large scale in both industry and academia, so it is desirable to have an apparatus that allows these assays to be performed in a convenient and inexpensive fashion. Because they are relatively easy to handle and low in cost, microplates are often used for such studies. Microplates typically consist of a plurality of individual wells formed of polymeric materials. Each well includes sidewalls and a bottom so that an aliquot of a sample may be placed within each well. The wells may be arranged in relatively close proximity in a matrix pattern, allowing samples to be studied individually or as a group. Common sizes for microplates include matrices having dimensions of 4×6 (24 wells) or 8×12 (96 wells), although larger microplates are also used that may include matrices of hundreds or even thousands of wells.

Typically, the materials used to construct a microplate are selected based on the samples to be assayed and the analytical techniques to be used. For example, the materials of which the microplate is made should be chemically inert to the components of the sample, and the materials should be impervious to radiation or heating conditions to which the microplate is exposed during the course of an experiment. Thus, a microplate used in assaying samples by UV absorption should have a UV permeable bottom sheet so that a substantial amount UV radiation can pass through each well and interact with the sample without being absorbed by the well bottom.

Despite the potential advantages of employing microplates having UV permeable bottom sheets, there has been limited progress in manufacturing such microplates. One problem in designing these microplates relates to the polymeric materials that are typically used for microplate construction. In particular, these polymeric materials usually have relatively high UV absorption probabilities. Absorption of UV radiation by the polymeric materials results in the chemical and physical degradation of the microplates. Therefore, to prolong the lifetime of these microplates, UV stabilizers specifically designed to absorb UV radiation are often added to the polymeric materials. As a result, most known microplates have exceptionally high UV absorption probabilities, rendering them useless for experiments in which UV absorption of samples is used.

U.S. Pat. No. 5,487,872 to Hafeman et al. (Hafeman) discloses a microplate designed for assaying samples with UV absorption techniques. Hafeman discloses a variety of materials from which the bottom surface of the microplate wells may be formed, including TPX® 4-methylpentene-1 polymer as the preferred material (Mitsui Petrochemical Industries, Japan). However, it is believed that microplates using this material for the well bottoms may have limited sensitivity in certain biochemcial experiments. For example, in nucleic acid studies, UV absorption in a range between approximately 260 nm to approximately 280 nm is studied, but TPX® has a relatively high optical density in this wavelength range.

Microplates having a quartz bottom plate glued to a molded body have also been produced. However, the cost of these microplates is often more than two orders of magnitude higher than the cost of a microplate formed entirely from polymeric materials, precluding their use for most studies. In addition, the materials used to bond the quartz bottom plate to the microplate body may leach into samples contained within the wells of the microplate, contaminating the samples and compromising the reliability of the experimental results. Furthermore, over time, the strength of the bond between the bottom plate and the body may deteriorate and form leaks between sample wells.

Hence, it remains a challenge in the art to provide a microplate that is relatively inexpensive, comparatively durable and includes well bottoms having an acceptable optical density across the entire useful range of the UV spectrum.

SUMMARY OF THE INVENTION

In one illustrative embodiment of the invention, a microplate is provided that comprises a frame that forms sidewalls of at least one well and a first layer that forms a bottom of the at least one well. The first layer is formed from a plastic material having an average optical density no more than approximately 0.09 at a thickness of approximately 7.5 mils between wavelengths of approximately 200 nm and approximately 300 nm.

In another illustrative embodiment of the invention, a microplate is provided that comprises a frame and a sheet. The frame includes an upper portion and a lower portion that is contiguous with the upper portion. The upper portion of the frame defines sidewalls of at least one well. The sheet defines a bottom of the at least one well, and at least a portion of the sheet is disposed between the upper and lower portions of the frame.

In yet another illustrative embodiment of the invention, a method is provided for making a microplate having at least first and second wells, each of the first and second wells having sidewalls and a bottom. The method comprises steps of: (A) inserting a sheet of a first material into a mold cavity that includes sections shaped to form the sidewalls of the first and second wells so that the sheet is positioned to form the bottoms of the first and second wells, the first material having an average optical density that is no more than approximately 0.09 at a thickness of approximately 7.5 mils between wavelengths of approximately 200 nm and approximately 300 nm; (B) injecting a molten plastic material into the mold cavity; and (C) cooling the plastic material to form the microplate with the plastic material forming the sidewalls of the first and second wells and the sheet of the first material forming the bottom of each of the first and second wells.

In a further embodiment of the invention, a method is provided for forming a microplate. The method comprises steps of: (A) providing an upper plate defining sidewalls of at least one well, the upper plate having a lower surface; (B) adhering an intermediate layer to the lower surface of the upper plate; and (C) adhering a sheet of the first material to the intermediate layer so that the sheet of the first material forms a bottom of the at least one well.

In yet a further embodiment of the present invention, a method is provided for making a microplate having at least first and second wells, each of the first and second wells having sidewalls and a bottom. The method comprises steps of: (A) inserting a sheet of a material having at least one hole into a mold cavity that includes sections shaped to form the sidewalls of the first and second wells so that the sheet is positioned to form the bottoms of the first and second wells; (B) injecting a molten first plastic material into the mold cavity; and (C) cooling the first plastic material to form the microplate with the first plastic material forming the sidewalls of the first and second wells and the sheet of the first material forming the bottom of each of the first and second wells.

In still a further illustrative embodiment of the invention, a microplate is provided that comprises a frame that forms sidewalls of at least one well and a first layer that forms a bottom of the at least one well. The first layer is formed from a chlorotrifluoropolyethylene, such as Aclar® film, and may have an average optical density of no more than approximately 0.09 at a thickness of approximately 7.5 mils, or may have a larger value if copolymer(s) are incorporated therein.

BRIEF DESCRIPTION OF THE DRAWINGS

The various features and advantages of the present invention will be better understood and appreciated from the following detailed description of several illustrative embodiments of the invention when taken in conjunction with the accompanying drawings in which.

DETAILED DESCRIPTION OF THE INVENTION

Figure 1:
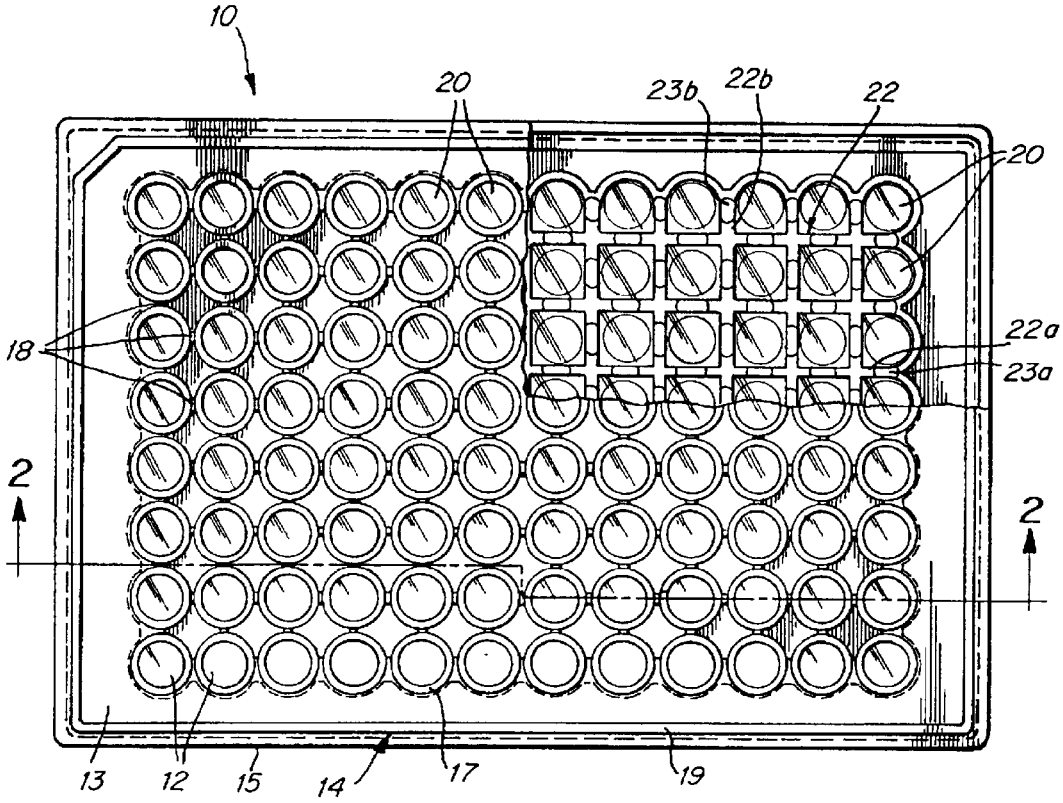
FIG. 1 is a partial top view and partial bottom view of a microplate in accordance with one embodiment of the present invention.
Figure 2:
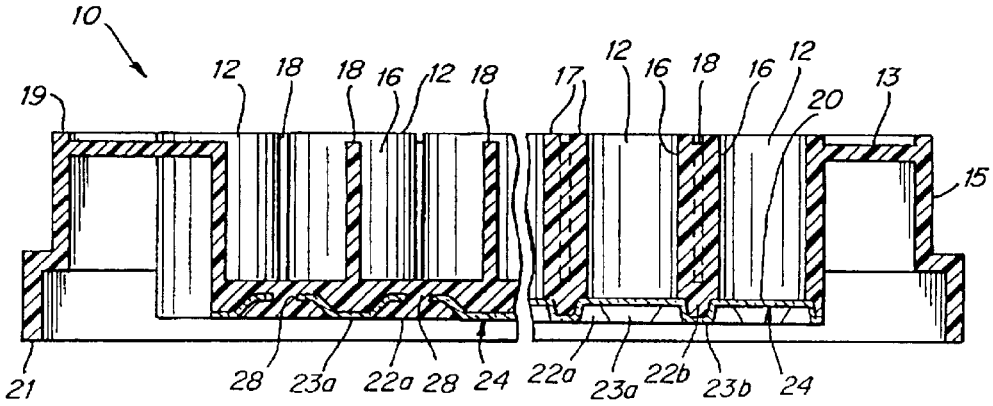
FIG. 2 is a fragmentary cross-sectional view of the microplate of FIG. 1 taken along the section line 2—2 in FIG. 1.

An illustrative microplate 10 in accordance with the present invention is shown in FIGS. 1 and 2, with FIG. 1 being a partial top and bottom views and FIG. 2 showing a cross-sectional view along line 2—2 of FIG. 1. The microplate 10 includes an array of wells 12, each of which may receive an aliquot of a sample to be assayed. In the embodiment shown, the microplate includes ninety-six wells arranged in a grid having a plurality of rows and columns. However, the present invention is not limited to this arrangement. The present invention can be implemented in any type of microplate arrangement (e.g., all established industry standards such as six, twenty-four, forty-eight, ninety-six, or more wells), and is not limited to any specific number of wells or any specific dimensions.

Figure 3:
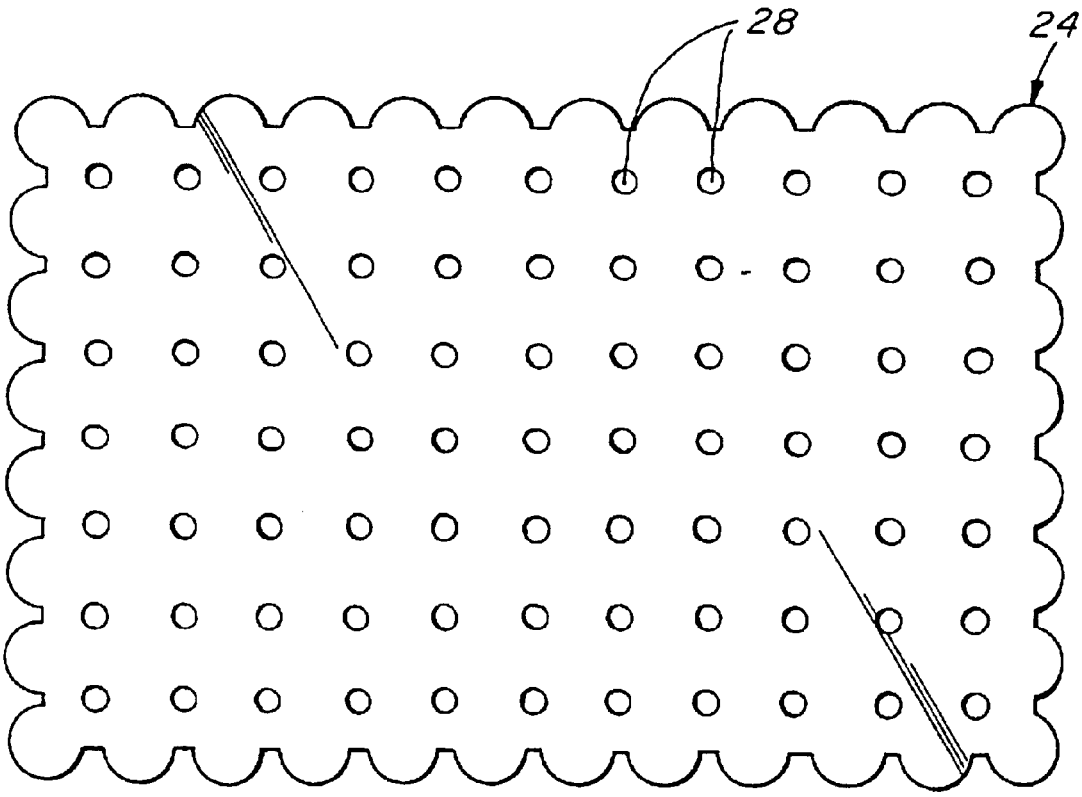
FIG. 3 is a top view of a UV permeable sheet in accordance with one embodiment of the present invention.

Each well includes a top rim 17, sidewalls 16 and a bottom 20. Since the microplate 10 is designed to be used for assaying samples by UV spectroscopy, the bottoms 20 are formed from a UV permeable material. In the embodiment shown in the figures, the bottoms 20 of all the wells are formed from a single sheet 24 of material. The sheet 24 may be rectangular, scalloped along the outer edges as shown in FIG. 3 to conform to the arrangement of the array of wells, or any other shape that is suitable for establishing the bottom 20 of each well.

UV permeation of a material can be measured in terms of optical density which is defined according to Beer's Law:

$$A(\lambda, t) = \log\left(\frac{P_0(\lambda)}{P(\lambda, t)}\right)$$

in which A is the optical density of the material, $\lambda$ is the wavelength of the radiation incident upon the material, t is the path length of the material through which the radiation passes, $P_0$ is the power of the radiation incident on the material at the wavelength $\lambda$, and P is the power of the radiation that passes the through the material at the wavelength $\lambda$ at the path length t. As can be seen from Beer's Law, the optical density of a material depends upon the wavelength of radiation and the path length of the radiation through the material. Therefore, it is convenient to define the UV permeability of a material in terms of the average optical density of the material at a particular thickness and between a specific range of wavelengths. As used herein, all references to a UV optical density of a material are intended to indicate the average optical density of the material assuming a thickness of approximately 7.5 mils and a wavelength range between approximately 200 nm and approximately 300 nm. It should be understood that the thickness of approximately 7.5 mils is used solely to provide a common basis for all references to UV optical density, and that no portion of the microplate of the present invention formed from a UV permeable material is limited to that thickness. The thickness of various elements of the microplate of the present invention can vary as described elsewhere herein.

Examples of UV permeable materials suitable for use in the present invention include polymeric materials such as polyolefins, fluoropolymers, polyesters, nonaromatic hydrocarbons, polyvinylidene chlorides and polyhalocarbons, such as polycholortrifluoroethylenes. It is to be understood that, as used herein, a polymeric material may be a homopolymer or a copolymer. Polyolefins may include polyethylenes, polymethylpentenes and polypropylenes, and fluoropolymers may include polyvinyl fluorides. Specific examples of these UV permeable materials include Kynar™ film (3M, Minneapolis, Minn.), KelF™ film (3M, Minneapolis, Minn.) and Aclar® film (Allied Signal, Morristown, N.J.). While particular UV permeable materials have been disclosed herein, it should be understood that this list is merely exemplary and not limiting.

As known to those skilled in the art, many polymeric materials have UV stabilizers incorporated therein to decrease the amount of UV radiation absorbed by the polymeric materials. Examples of UV stabilizers include, but are not limited to, hydroxybenzophenones, hydroxylphenyl benzotriazoles, hindered amines, organic nickel compounds, salicylates, cinnamate derivatives, resorcinol monobenzoates, oxanilides and p-hydroxybenzoates. Such UV stabilizers increase the optical density of the polymeric materials due to their relatively high UV absorption coefficients. Therefore, according to the present invention, UV permeable materials are preferably substantially free of UV stabilizers.

Figure 4A:
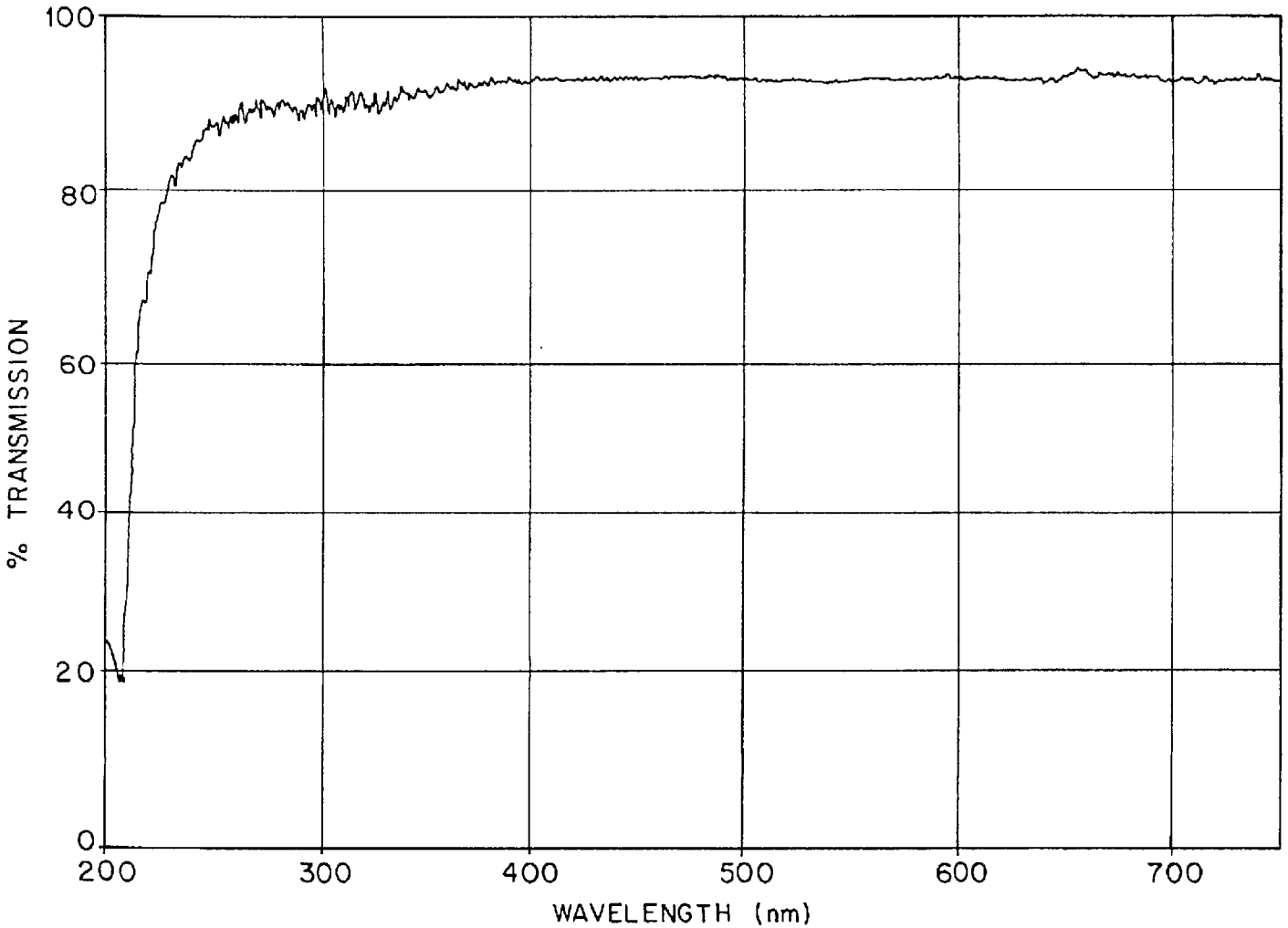
FIGS. 4A–4C are UV spectra of a 7.5 mil thick sheet of Aclar® film that can be used to form the bottom wells of a microplate according to the present invention, a 0.5 mil thick piece of Glad™ cling wrap, and a 14 mil thick piece of TPX® taken from a Hafeman microplate, respectively.
Figure 4B:
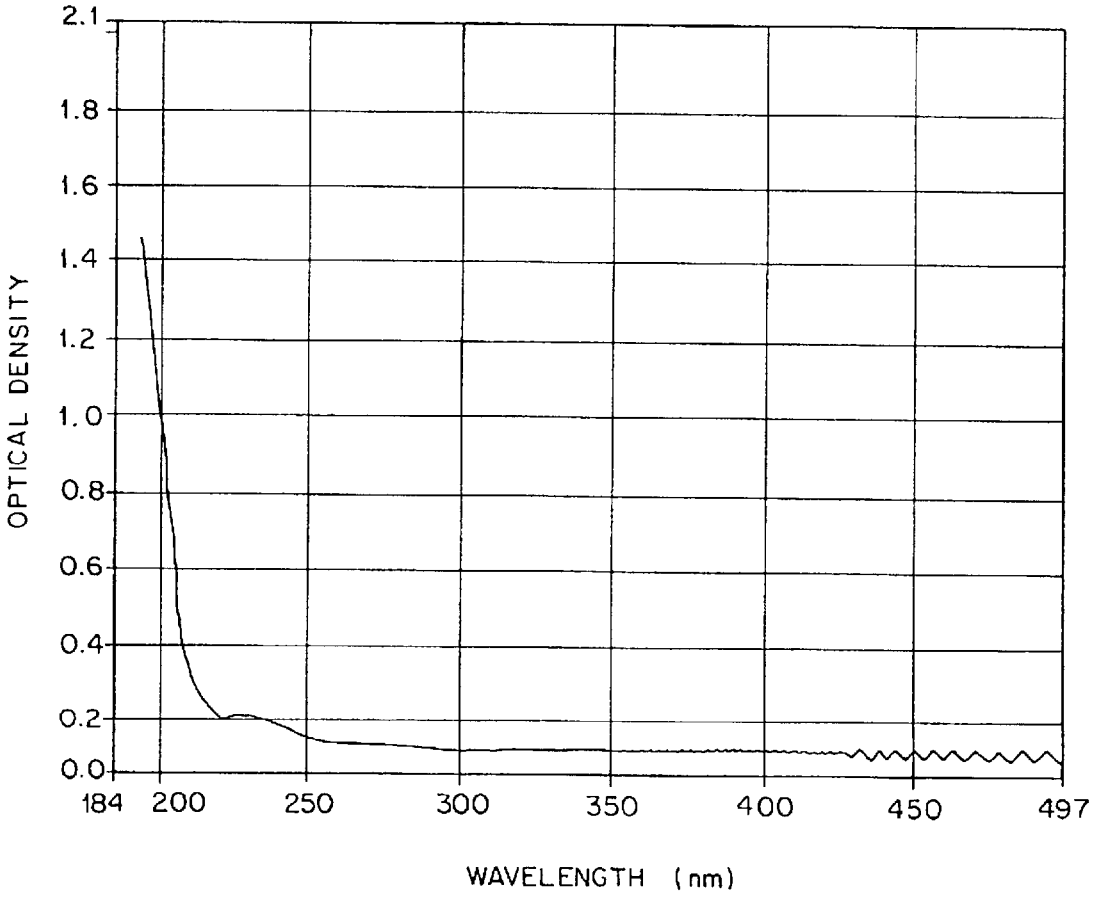
Figure 4C:
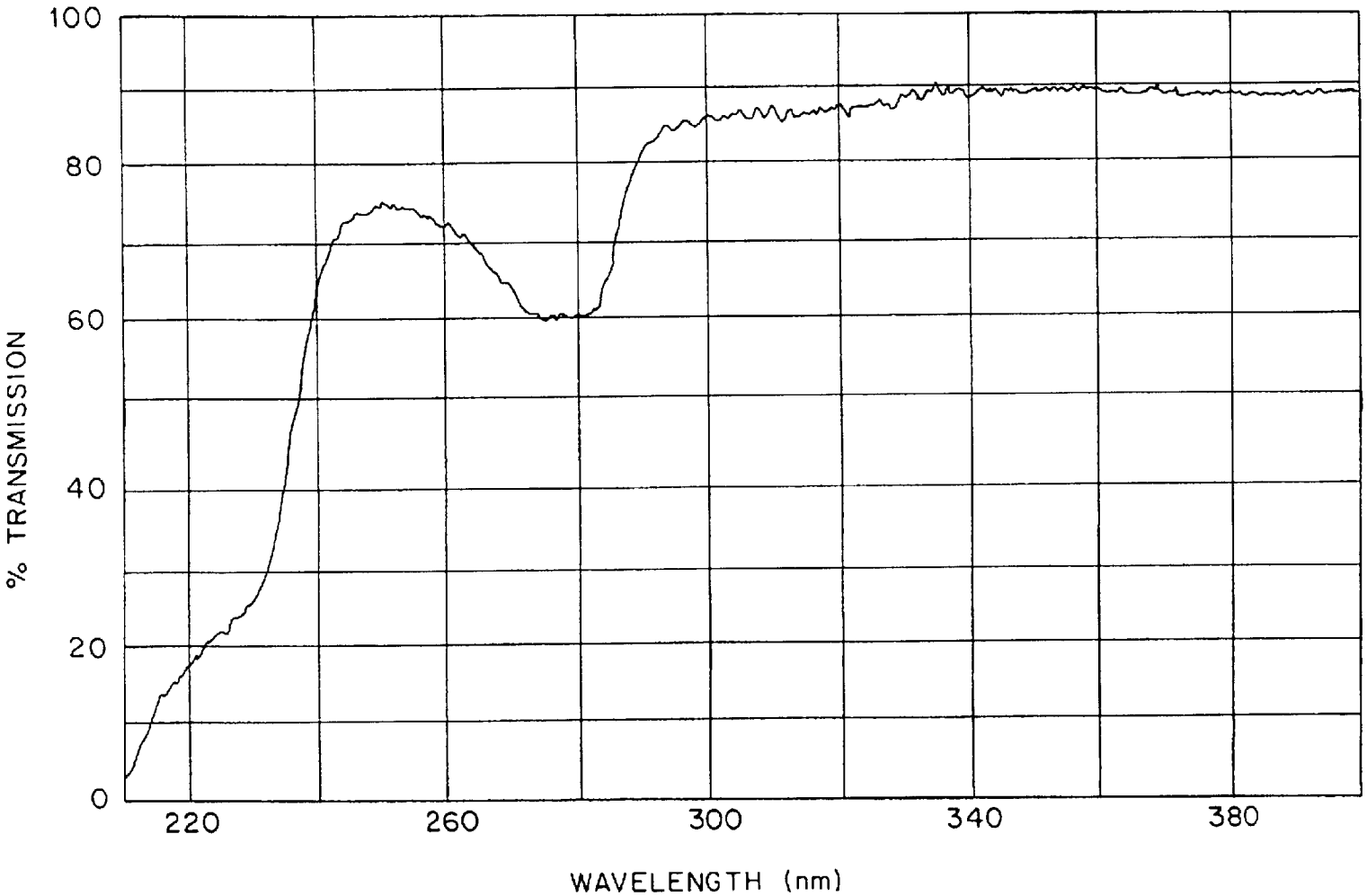

In one embodiment, Aclar® film is used as the UV permeable material. The UV absorption spectrum of a 7.5 mil sheet of Aclar® film removed from a microplate in accordance with the present invention is shown in FIG. 4A. The UV absorption spectrum of a 0.5 mil thick piece of Glad™ cling wrap is shown in FIG. 4B, and FIG. 4C depicts the UV absorption spectrum of a 14 mil thick piece of TPX® taken from a Hafeman microplate. The spectra shown in FIGS. 4A–4C were each taken with an AVIV 14DS spectrophotometer using a ⅓ slit height bandpass of 1.0 nm and a 2 mm by 4 mm aperture.

The average optical density for the wavelength range between approximately 200 nm and approximately 300 nm for the 0.5 mil Glad™ cling wrap piece and the 14 mil TPX® piece are 0.27 and 0.3, respectively. The UV optical density of the 7.5 mil sheet of Aclar® film is approximately 0.09. While a direct comparison of UV absorption was not made between these materials at a constant thickness, it is known that the optical density of a material [decreases] *increases* as the thickness of the material is increased. Therefore, it is believed that a sheet of Aclar® film having a thickness of 0.5 mil would have a UV optical density of less than 0.27 and that a sheet of Aclar® film having a thickness of 14 mils would have a UV optical density of less than 0.3. Furthermore, while the UV optical density of a 7.5 mil sheet of Aclar® film (approximately 0.09) has been disclosed, it is to be understood that the UV optical density of a sheet of Aclar® film, or any other material appropriate for use as sheet 24, may be varied by incorporation of a copolymer or copolymers that are capable of adsorbing UV radiation in a wavelength range between approximately 200 nm and approximately 300 nm. Chlortrifluoropolyethylene, such as Aclar® film, being a particularly preferred material for inclusion in the microplate, is not limited to an average optical density of approximately 0.09 and may have a larger value, such as by the incorporation of copolymer(s), while still being within the invention contemplated herein.

In addition to having a comparatively low UV optical density, Aclar® film has the property of decreased solvent transmission at temperatures below approximately 250° F.–300° F., depending upon the solvent and the thickness of the sheet of Aclar® film. A sheet of Aclar® film may have one or both sides corona treated by exposure to ozone formed by an electric discharge in the presence of oxygen. However, corona treatment is not believed to provide any particular advantage for use in the present invention so that a sheet of Aclar® film that has not been corona treated may also be used.

To minimize absorption of UV radiation, well bottoms 20 in the microplate of the present invention preferably have a average optical density, measured at wavelengths between approximately 200 nm and approximately 300 nm, of less than approximately 0.09. In some embodiments, the thicknesses of the well bottoms of the microplate may vary, resulting from a change in crystallinity of portions of sheet 24 due to the diverse temperature range to which sheet 24 may be exposed during the manufacture of microplate 10. Since the variation in well bottom thickness can introduce errors into sample assays, the difference in the average optical density of any two wells, measured at wavelengths between approximately 200 nm and approximately 300 nm, is preferably no greater than approximately 0.09. However, where the well bottoms 20 are formed from chlorotrifluoropolyethylene and copolymer(s), the optical density between wavelengths of approximately 200 nm and approximately 300 nm is not limited to approximately 0.09 and is still within the invention contemplated herein.

Many UV permeable materials are also capable of transmitting at least approximately 90% of visible light at the thicknesses appropriate for the well bottoms 20 as discussed below. Therefore, a microplate of the present invention can also used for assays that use visible light (e.g., fluorescence experiments). Aclar® film is also believed to be an advantageous material for forming a microplate to be used in this manner because of its solvent resistance.

To reduce the amount of UV radiation absorbed by well bottoms 20, it is desirable to minimize the thickness of sheet 24. However, if sheet 24 is too thin, solvents and other components of the same stored in wells 12, such as dimethyl sulfoxide (DMSO), may pass through sheet 24 when microplate 10 is heated during use. It has been found that, to minimize UV absorption while preventing solvent transmission, sheet 24 should have a thickness of less than approximately 14 mils. Preferably, the thickness of sheet 24 is from approximately 2 mils to approximately 9 mils and more preferably from approximately 5 mils to approximately 8 mils. Another advantage of minimizing the thickness of sheet 24 is that, when microplate 10 is constructed according to the molding processes discussed below, stresses between the molded materials and warping of microplate 10 are reduced or eliminated.

As seen from the top view of FIG. 1, microplate 10 includes a frame 14 that supports the wells 12. Frame 14 includes outer walls 15 and a top planar surface 13 extending between the outer walls and the wells 12. In the embodiment shown, the frame is rectangular in shape. However, it should be understood that the frame 14 can be provided in any number of other geometrical shapes (e.g., triangular or square) depending on the desired arrangement of the wells 12. Support walls 18 connect the sidewalls 16 of adjacent wells, as shown in FIGS. 1–2. In the illustrative embodiment shown, the wells 12 have circular cross-sections in a plane parallel to the planar surface 13. However, the invention is not limited in this respect, and it should be understood that wells 12 may be provided in a number of alternate configurations having different cross-sectional shapes, e.g., rectangles, squares and triangles.

In one embodiment of the invention, the outer wall 15 that defines the outer periphery of the frame 14 extends below the bottoms 20 of the wells. As shown in FIG. 2, the outer wall 15 has a bottom edge 21 that extends below the bottom 20 of the wells, so that when placed on a support surface, the microplate is supported by the bottom edges 21 with the well bottoms 20 being raised above the support surface to protect them from damage. In the configuration shown in FIGS. 1 and 2, each outer wall 15 also has a rim 19 to accommodate the skirt of a microplate cover (not shown).

Many UV permeable materials, including polychlorotrifluoroethylenes and fluoropolymers, have relatively low surface tensions and do not adhere well to other materials. Thus, when such materials are used to form the well bottoms in a microplate, there is a risk that the UV permeable material can peal or separate from the rest of the microplate during use. To increase the adhesion between UV permeable sheet 24 and the sidewalls 16, the microplate of the present invention is constructed so that the material of which the sidewalls 16 are formed is adhered to both the upper and lower surfaces of the sheet 24. In one embodiment, this is achieved by placing holes 28 within the sheet 24 (FIG. 3) so that during the molding process described below, a molten plastic material that forms the sidewalls 16 on the upper surface of sheet 24 also passes through the holes 28 and adheres to the lower surface of sheet 24. Aclar® film has a relatively low surface tension even when compared to certain other UV permeable materials. Thus, adhesion of the plastic material to both sides of a sheet of Aclar® film can be particularly advantageous.

In the embodiments shown in the figures, the microplate 10 is provided with a plurality of ribs 22, each of which is formed from the plastic material during the molding processes described below. Each of the ribs 22 is contiguous with the sidewalls 16 of an adjacent pair of the plurality of wells 12 and extends below the bottom of its adjacent well bottoms. A portion of each rib is formed by molten material that passes through the holes 28 in the sheet 24 during the molding process. This portion of each rib is disposed below and adheres to the lower surface of the sheet 24. However, another portion of each rib is formed by molten material that does not pass through the sheet, but rather, forces the sheet 24 against the section of the mold that defines the rib. This portion of each rib is disposed above the sheet 24, which is distorted to accommodate this portion of the rib. The distorted portions of sheet 24 form a plurality of segments 23 disposed between adjacent well bottoms. A portion of each of the segments 23 is offset from the bottoms of its adjacent wells, such that no plane passing through the bottoms of adjacent wells passes entirely through a segment 23 of the sheet extending therebetween. For embodiments of the microplate 10 in which it is desirable to reduce or eliminate the transmission of radiation between adjacent wells as discussed below, the molten material that forms the ribs and the sidewalls of the microplate can be formed of a material that is impermeable to the type of radiation used in the assay (e.g., UV or visible light). However, it should be understood that the rib grid arrangement is not necessary, and that the microplate 10 can be formed with a different bottom structure that adheres to the lower surface of sheet 24 to securely attach the sheet 24 to the upper portion of the microplate.

In the embodiment shown in FIGS. 1 and 2, the ribs 22 are oriented in a grid arrangement with some of the ribs 22a extending in rows parallel to the length of the microplate, and others 22b extending in columns perpendicular to the length of the microplate. Segments 23a are disposed along ribs 22a, and segments 23b are disposed along ribs 22b. The grid pattern of ribs 22 is shown because this arrangement is simple and economical to manufacture. However, as discussed above, other arrangements may be used.

In one embodiment of the invention, frame 14, wells 12, support walls 18 and ribs 22 are made of a UV impermeable material to reduce or eliminate interference from transmission of radiation between adjacent wells. As used herein, a material is considered to be UV impermeable if it has a UV optical density greater than approximately 0.25. In general, UV impermeable materials may reflect or absorb UV radiation. Therefore, a UV impermeable material may be formed of a base material that can be UV permeable, that further includes solid pigments that reflect UV radiation (e.g., titanium dioxide, zinc oxide, zinc sulfide and thiopene) or solid pigments that absorb UV radiation (e.g., carbon black). Alternatively, materials which have the inherent property of high UV absorbance may be used. Such materials include, for example, aromatic hydrocarbons and hydrocarbons with extended portions of conjugated unsaturation. It should be understood that UV impermeable materials may also be capable of reducing or eliminating the transmission of visible light between adjacent wells which can reduce interference due to transmission of visible light between wells when the microplate is used for assays that use visible light. Alternatively, if the microplate of the present invention is to be used with an assay that uses visible light, the portions of the microplate other than sheet 24 can be formed from a material impermeable to visible light.

The sheet 24 and the other portions of microplate 10 can be made of one or more moldable plastics using any of a number of standard fabrication techniques, e.g., injection molding, extrusion, calendering and injection compression. As used herein, the term plastic material denotes a material comprising a polymerization product incorporating repeating monomer units. Such a polymerization product may be a homopolymer or a copolymer.

One method of forming a microplate in accordance with the present invention is described making reference to FIGS. 5–9B. Initially, the sheet 24 is formed using a standard fabrication technique, such as any of the ones listed above, into the desired geometrical shape. In the embodiment shown in FIG. 3, the UV permeable sheet 24 is planar and has the plurality of holes 28 extending therethrough. Although depicted in FIG. 3 as being circular, holes 28 may have any shape (e.g., slits, rectangles, squares) so long as they are capable of allowing the molten material to flow therethrough and adhere to the upper and lower surfaces as described below. However, the holes 28 should not be large enough to overlap with well bottoms 20 so that leaking through the holes 28 is avoided.

Figure 5:
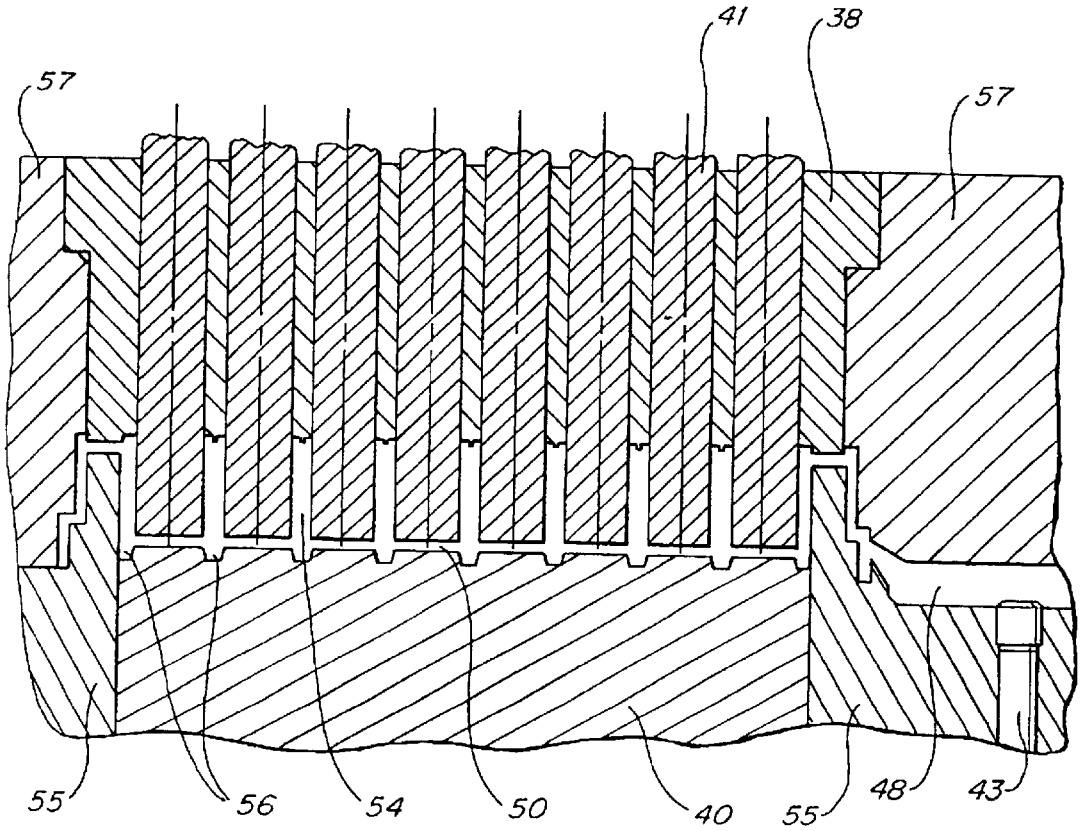
FIG. 5 is a fragmentary cross-sectional view of a mold and mold cavity in which one embodiment of a microplate of the present invention is formed.

In fabricating the remainder of the microplate, a two-piece mold can be used having a well-mold piece 38 and a rib-mold piece 40 as shown in FIG. 5. Rib-mold piece 40 is placed within a mold piece opening formed by outer mold support piece 55, and well-mold piece 38 is placed within a mold piece opening formed by outer mold support piece 57.

Figure 6:
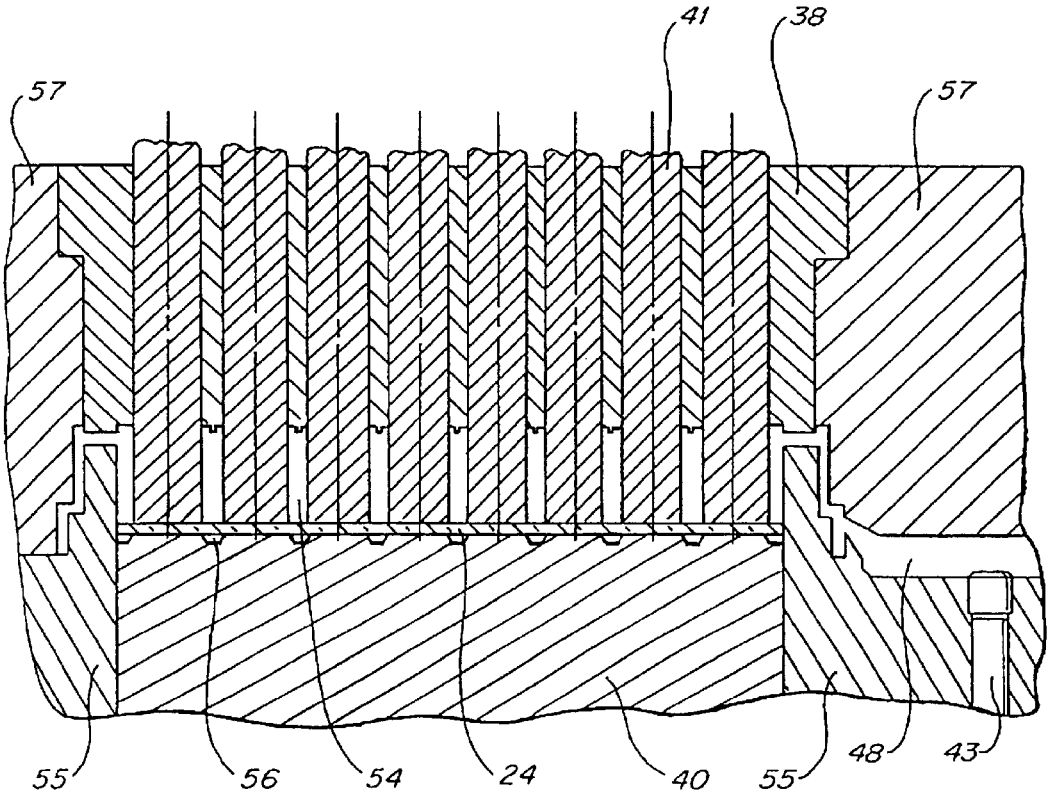
FIG. 6 is a fragmentary cross-sectional view similar to FIG. 5, but showing the sheet of FIG. 3 positioned in the mold cavity.
Figure 7:
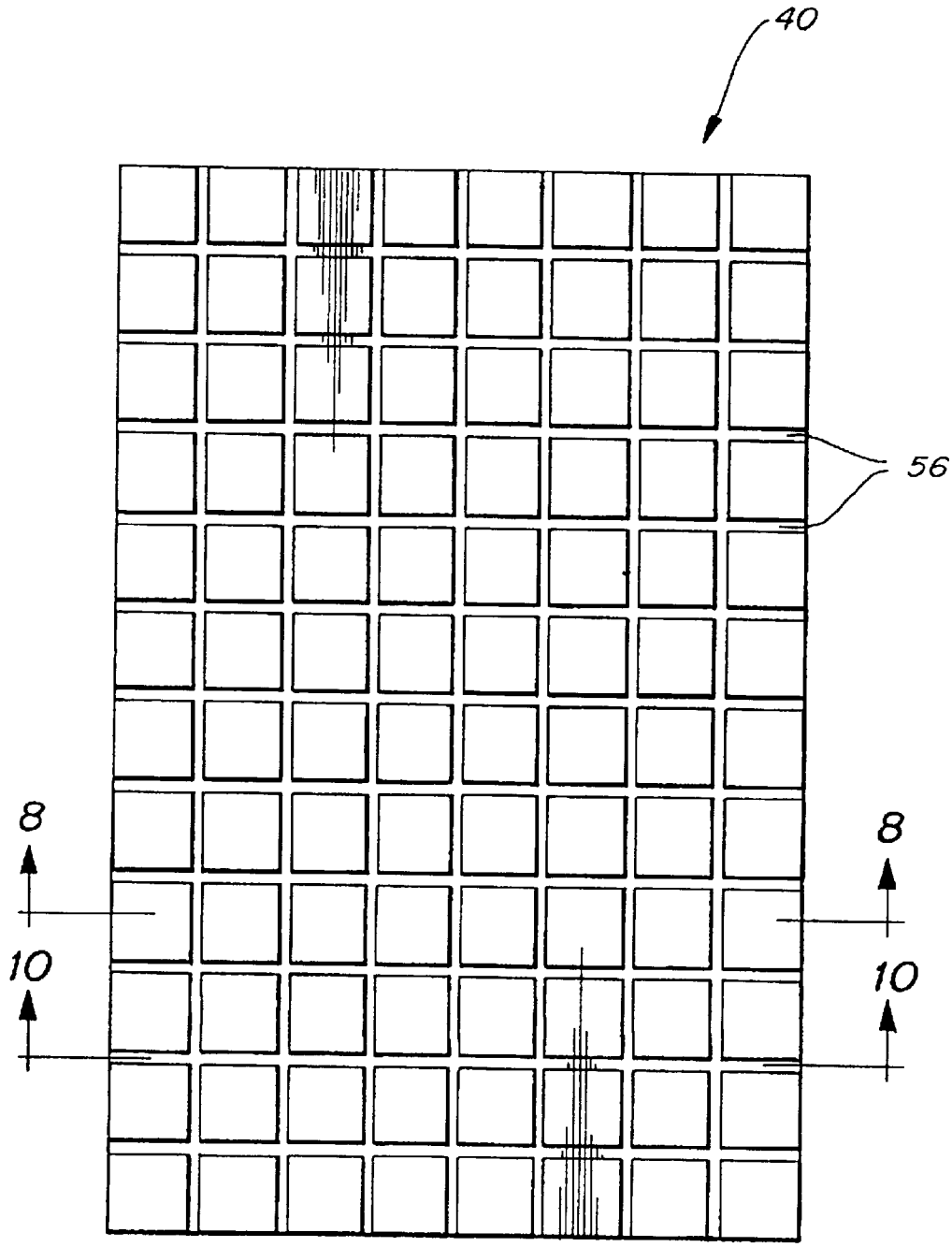
FIG. 7 shows a top view of a rib mold piece according to the present invention.

The sheet 24 that will ultimately form the well bottoms 20 and segments 23 is inserted into the cavity 50 of the rib-mold piece 40 shown in FIG. 6. The well-mold piece 38 is then mated with the rib-mold piece 40, enclosing the sheet 24 therebetween. The two mold pieces form a chamber 54 that has a shape that conforms to the final shape of the microplate 10. Corings or pins 41 prevent the molten material from entering into the area that will form the open areas of wells 12. Pins 41 can be an integral part of well-mold piece 38. Alternatively, pins 41 may not be a permanent part of well-mold piece 38 so that, subsequent to fabricating microplate 10, pins 41 may be removed from microplate 10 without removing well-mold piece 38 from microplate 10. The rib-mold piece 40 includes channels 56 (FIGS. 5–7) that define the regions where the ribs 22 and segments 23 will be formed. Similarly, the portion of the chamber 54 defined by the well-mold piece 38 includes sections that define the shape of the frame 14, well sidewalls 16, support walls 18 and the remaining portions of the microplate that are disposed on the opposite side of the sheet 24 from the ribs 22 and segments 23. It should be understood that alternate arrangements of the rib-mold and well-mold pieces can also be employed that would enable the formation of a microplate having the same configuration. Furthermore, different arrangements of the rib-mold and well-mold pieces can be used to form microplates having different configurations. For example, since the microplate 10 need not include the ribs 22, a mold piece may be used that does not include the continuous channels 56. Instead, such a mold piece may have discrete grooves disposed such that, when the sheet 24 is inserted within the mold the holes 28 are disposed above the slots or grooves so that the molten plastic material can flow through the holes 28 and adhere to the lower surface of sheet 24.

The sheet 24 is positioned in the mold cavity 54 so that one of the holes 28 is disposed at each row/column intersection of channels 56, which correspond to locations where the rows and columns of ribs 22 will intersect and pass entirely through sheet 24. The material that will form the upper portion of the microplate and the ribs is then injected in a molten state at high pressure and high temperature into the chamber 54 through an injection gate 48 in the well-mold piece 38. The mold cavity 54 does not provide any path for the molten material to pass from the sections of the cavity formed by the well-mold piece 38 into the channels 56, except through the holes 28 or by distorting and forcing the sheet 24 into the channels 56 due to the high pressure of the molten material. Therefore, upon injection into the chamber 54, the molten material partially fills the channels 56 by passing through holes 28, with the other portions of the channels 56 being filled by the sheet 24 being forced into the channels 56 by the molten material from above. It should be understood that it is not necessary for the molten material to distort the sheet 24 or fill the channels 56 to ensure that the sheet 24 is secured. All that is required is that the molten material pass through holes 28 and adhere to the lower surface of the sheet 24.

As the molten material cools in chamber 54 to form microplate 10, the cooled material may contract and partially adhere to rib-mold piece 40. Therefore, one or more knock-outs 43, shown in phantom, may be used to apply pressure against microplate 10 to remove it from rib-mold piece 40. Alternatively, knock-outs 43 may be located in well-mold piece 38 or in both piece 38 and piece 40. Alternatively, a stripper ring may be used to remove microplate 10 from mold piece 38 or mold piece 40.

Figure 8A:
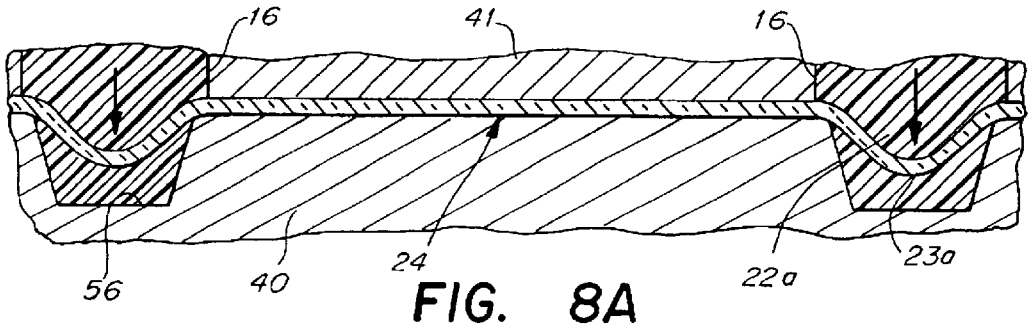
FIGS. 8A–8C depict partial cross-sectional views of the formation of a microplate using a molding process according to the present invention.
Figure 8B:
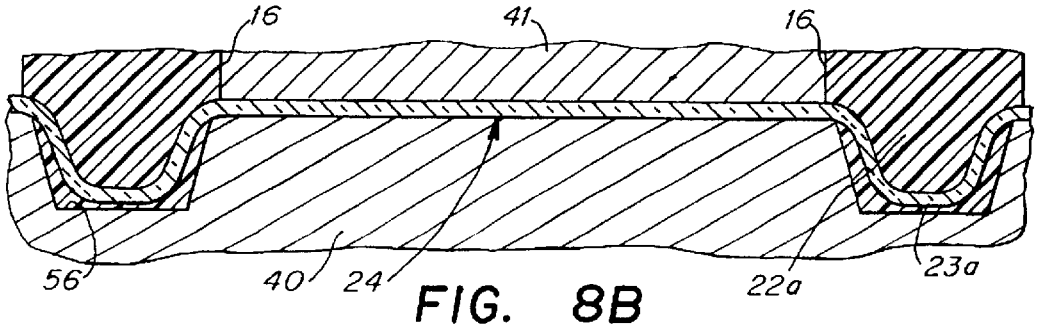
Figure 8C:
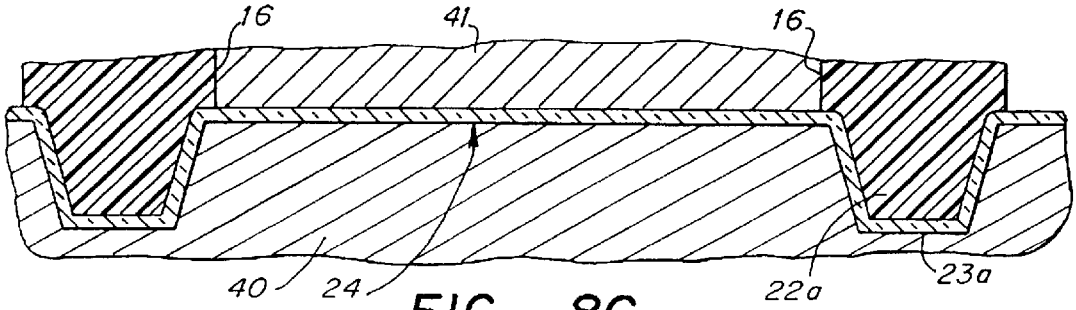
Figure 9A:
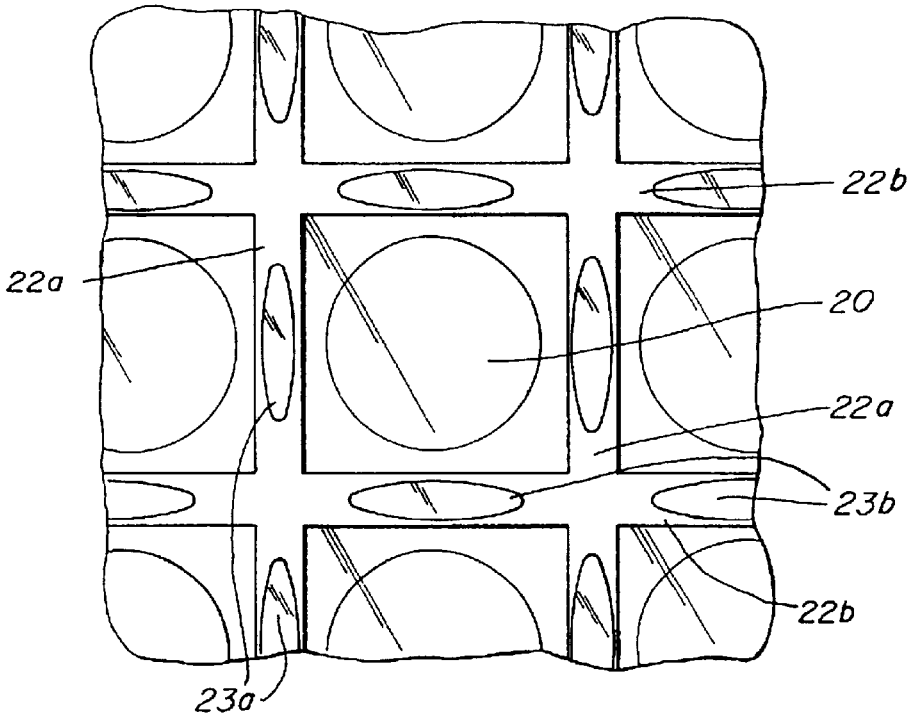
FIGS. 9A–9B show bottom views of the formation of a microplate corresponding to FIGS. 8B–8C, respectively.
Figure 9B:
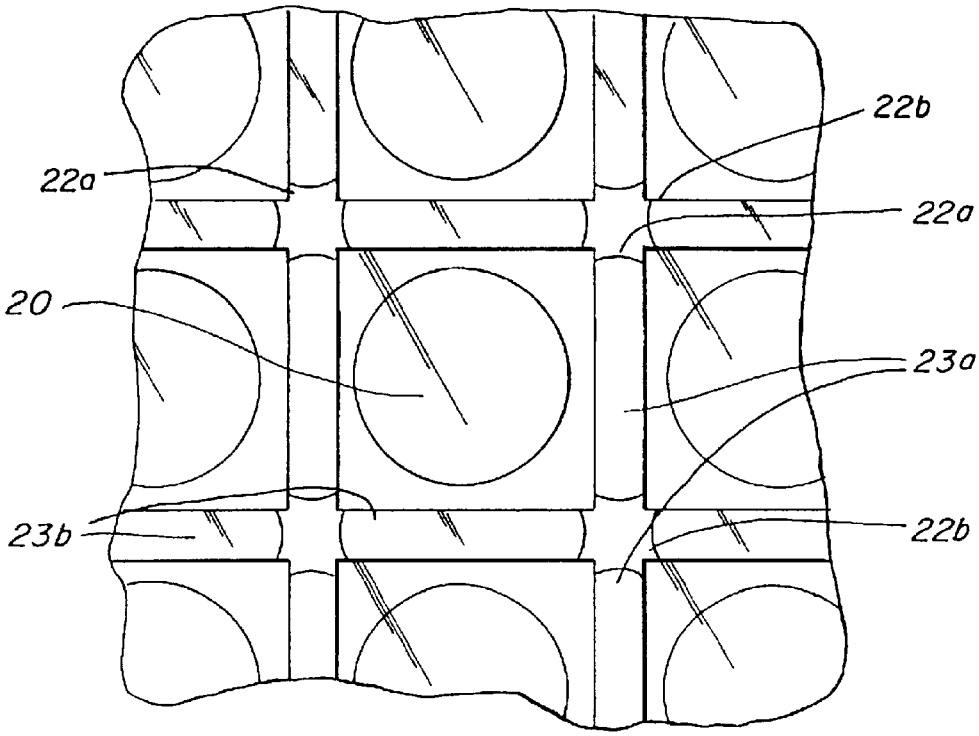
Figure 10A:
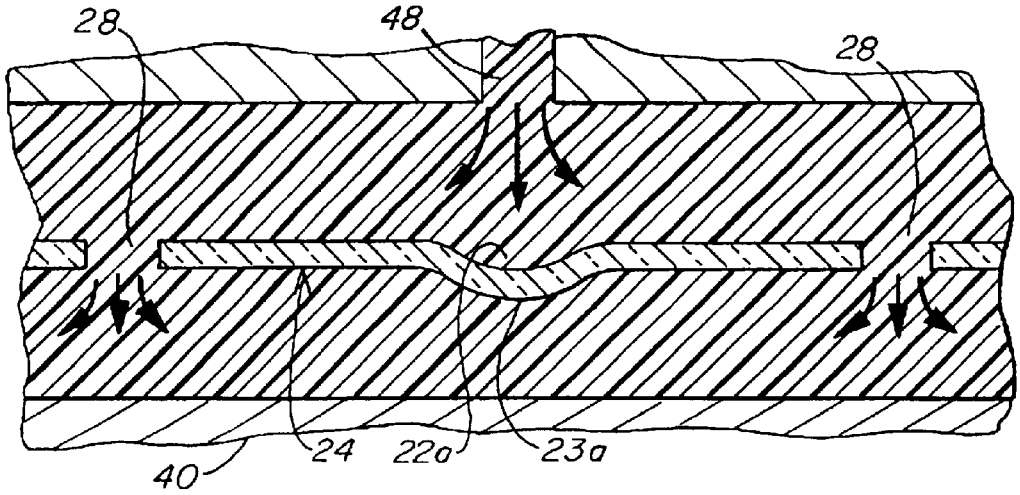
FIGS. 10A–10B depict alternate partial cross-sectional views of the formation of a microplate using a molding process according to the present invention.
Figure 10B:
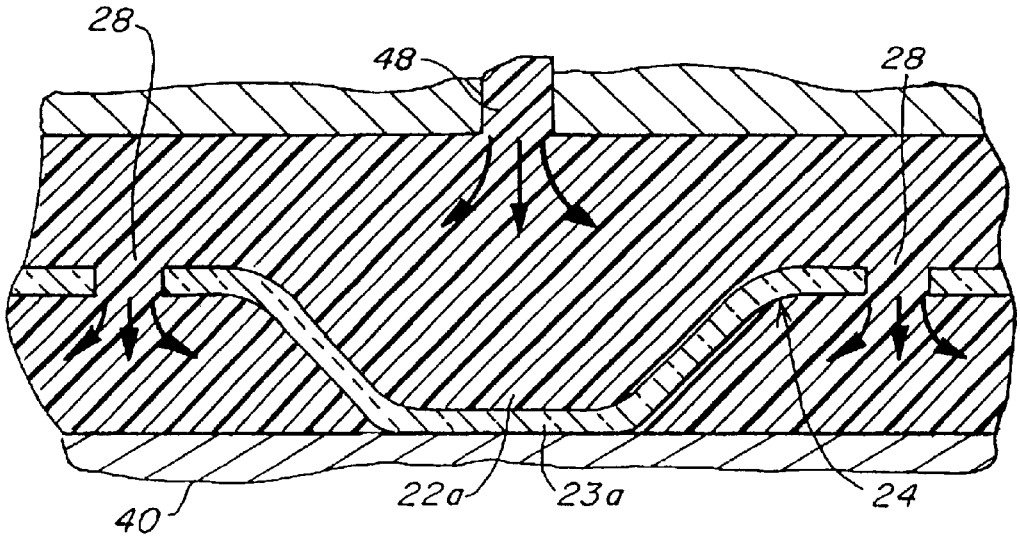

FIGS. 8A–10B demonstrate a process for fabricating a microplate using the mold arrangement shown in FIG. 6 and the molding process described above. FIGS. 8A–8C depict partial cross-sectional views, taken along line 8—8 of FIG. 7, of the mold arrangement during different stages of the injection molding process and FIGS. 9A–9B show bottom views of the stages of the molding process depicted in FIGS. 8B–8C, respectively. In addition, FIGS. 10A–10B depict partial cross-sectional views of the microplate fabrication process taken along line 10—10 of FIG. 7.

FIGS. 8A and 10A show the initial distortion of film 24 as the molten material is injected through injection gate 48, demonstrating that, as film 24 is distorted, ribs 22a and segments 23a begin to form. FIG. 10A demonstrates the flow paths of the molten material, including the molten material that exerts pressure on the film 24 to distort it and the molten material that passes through holes 28 and into channels 56 beneath film 24. FIG. 10B shows rib 22a and segments 23a that result. FIGS. 8B–8C and 9A–9B, respectively, depict intermediate and final stages in the molding process.

Figure 11A:
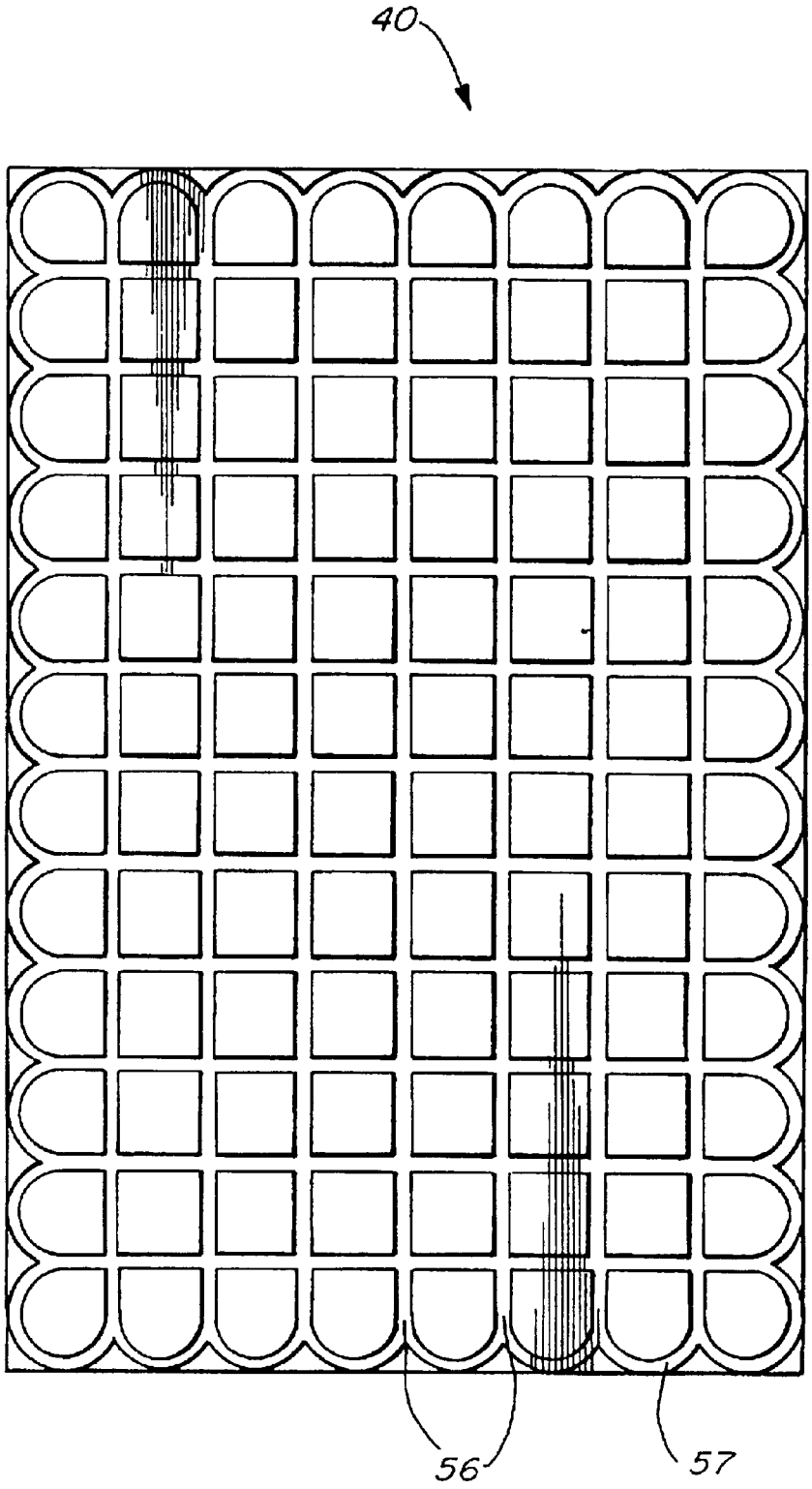
FIGS. 11A–11B are top views of two embodiments of portions of a mold in accordance with the present invention.
Figure 11B:
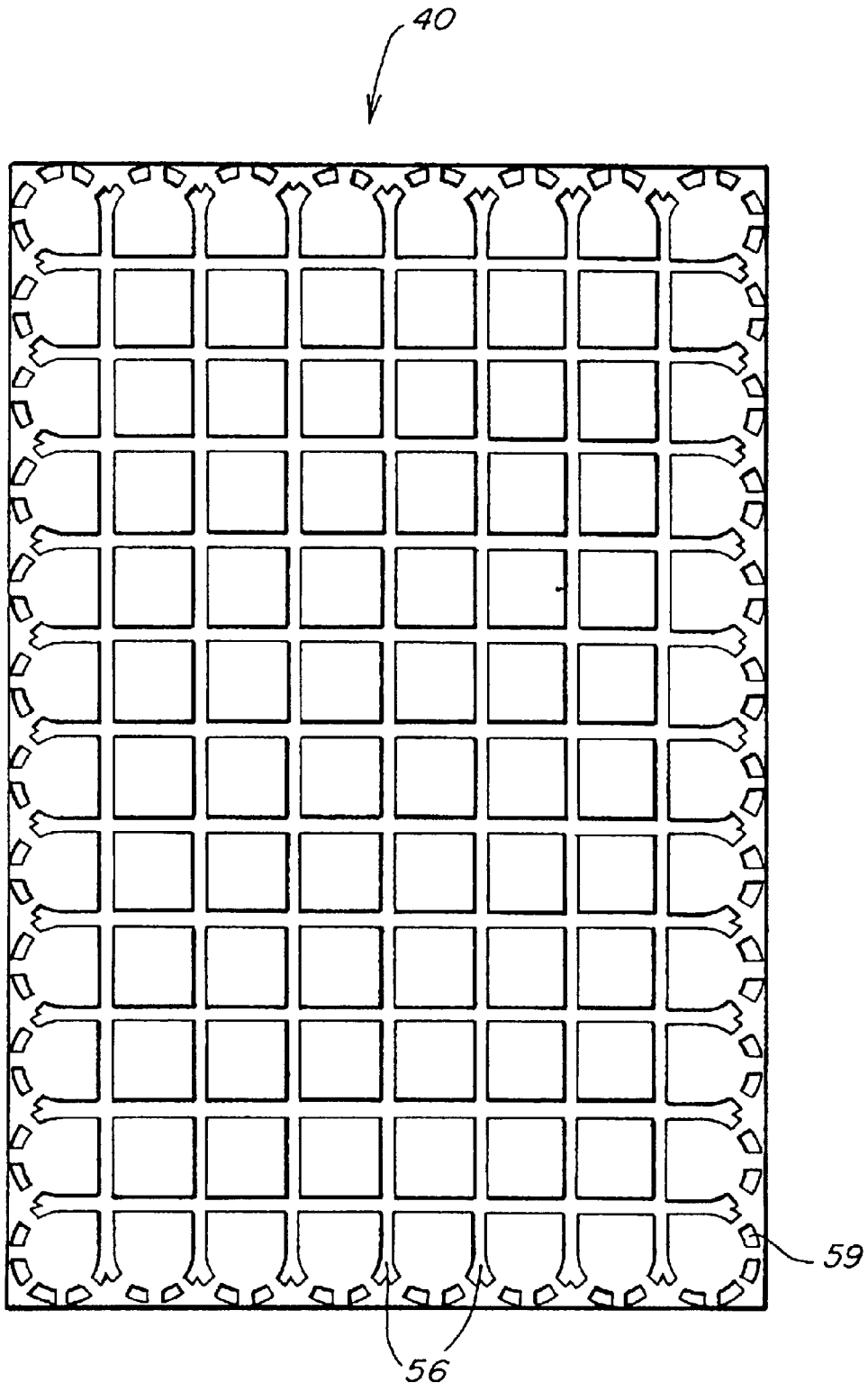
Figure 12A:
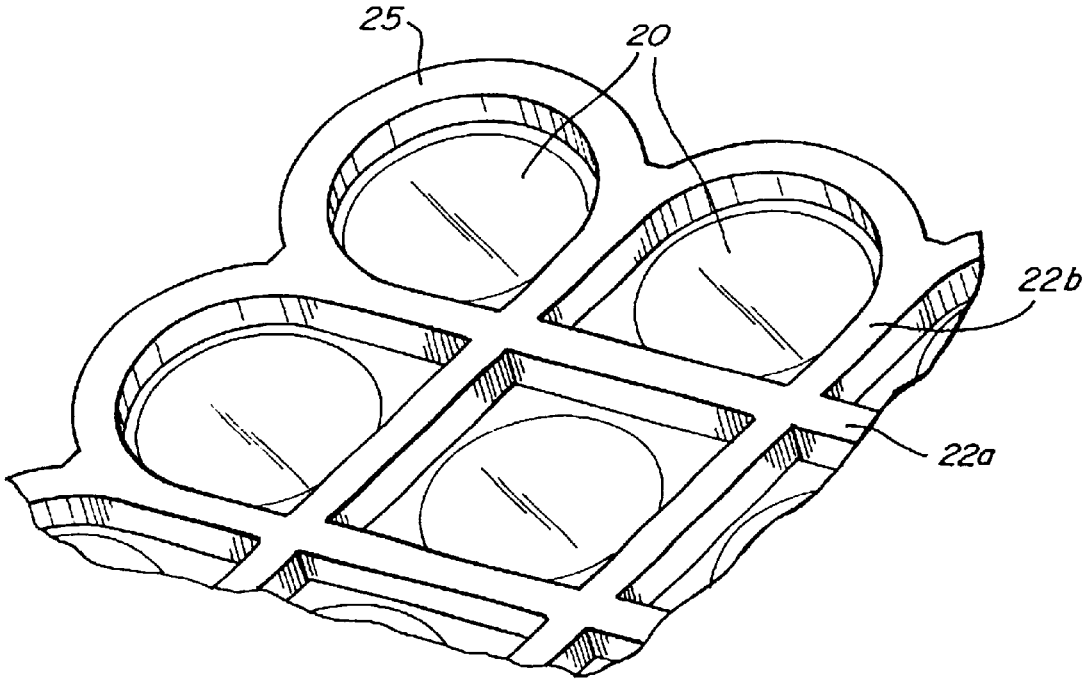
FIGS. 12A–12B are partial perspective views of embodiments of a microplate made using the rib mold pieces of FIGS. 11A and 11B, respectively.
Figure 12B:
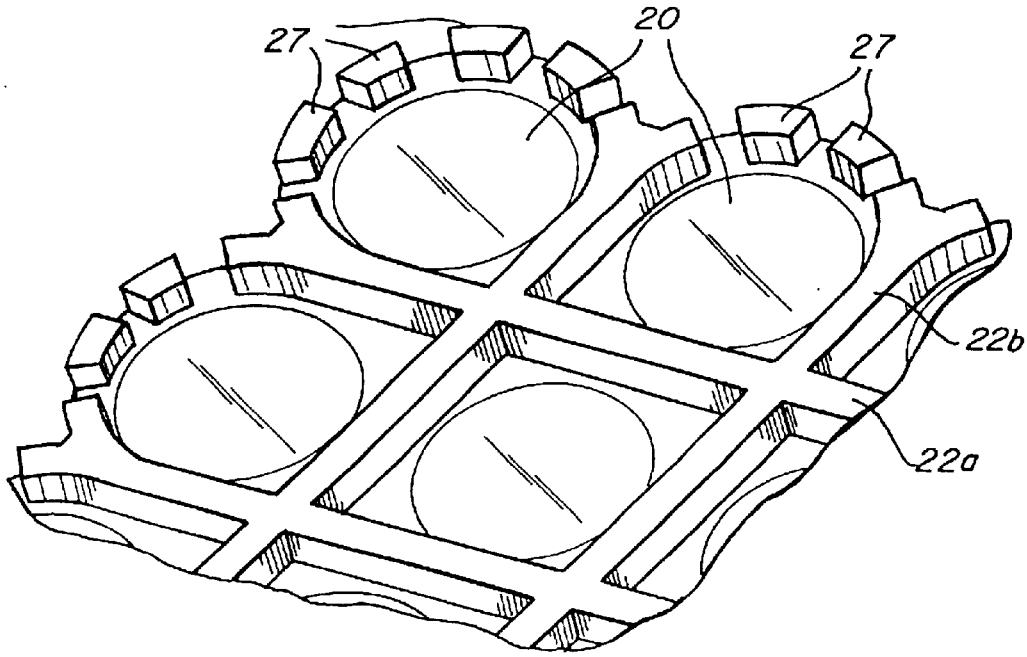

When the rib mold piece 40 shown in FIG. 5 is used, the molten material does not flow under the outer edges of sheet 24 during the molding process. To ensure that the molten material strongly adheres to both sides of the outer edges of the sheet 24, the mold piece 40 may include additional features 57 or 59 as shown in FIGS. 11A–11B disposed within mold piece 40 such that, when the sheet 24 is positioned within rib mold 40, the outer edges of sheet 24 partially overlap the features 57 or 59. The portion of the features 57 or 59 that is not located below the outer edges of the sheet 24 allows the molten material to flow around and beneath the outer edge of sheet 24 during the molding process. As shown in FIGS. 12A–12B, the resulting microplate 10 includes cleats 25 and 27 that adhere to the lower surface of sheet 24 to prevent the outer edges of sheet 24 from peeling away from the sidewalls 16.

The specific temperature and pressure at which the molten material is injected into the mold varies depending upon the particular material used. The pressure of the molten material should be sufficient to allow the molten material to pass through holes 28. The temperature should exceed the melting point of the molten material and allow the molten material to flow easily without altering its chemical composition. However, for embodiments in which the molten material is a UV impermeable material, the temperature and pressure should not be so high that the molten material undergoes mixing with the UV permeable sheet, resulting in unusable wells having UV impermeable bottoms, or bottoms with a UV permeable area that is substantially reduced. Generally, mixing of the UV impermeable molten materials and the sheet does not occur due to the relatively high melting point of most UV permeable materials. The table below provides examples of suitable parameter ranges for injection conditions of some exemplary plastic materials appropriate for use in molding processes according to the present invention. The temperatures and pressures of the molten materials are represented in units of degrees Fahrenheit and pounds per square inch gauge, respectively.

| Material | Temperature (° F.) | Pressure (psig) |
|---|---|---|
| polystyrene | 420–450 | 1200–1500 |
| polyolefin | 420–450 | 1200–1500 |
| polyacrylonitrile | 440–540 | 1200–1600 |
| acrylic | 380–480 | 1200–1600 |
| polyester | 480–550 | 1200–1800 |
| polycarbonate | 550–600 | 1400–2000 |
| polymethylpentene | 500–580 | 1200–1600 |

Spectrophotometers and other optical devices have been developed for use with microplates in the standard sizes. To reduce manufacturing costs, it is desirable to use a single mold to produce all microplates at a particular size. Furthermore, it may also be desirable to use a single mold to make microplates from different molten materials. However, different molten materials may shrink by different amounts upon cooling, so the final dimensions of microplates formed from a single mold may vary depending upon the molten material. Because polystyrene is commonly used to construct microplates, molds are often designed considering the mold shrinkage of polystyrene. The term mold shrinkage herein denotes the amount by which a material shrinks upon cooling. Therefore, in one embodiment of the present invention, additives may be incorporated into the molten material to produce a composite material having the mold shrinkage of polystyrene. Typically, the composite material includes from approximately 30% to 50% filler by weight. For example, a composite having approximately the same mold shrinkage as polystyrene can be formed from polypropylene and approximately 40% by weight mineral talc.

While the molten material may undergo appreciable shrinkage upon cooling, sheet 24 usually shrinks by a relatively small amount. As a result, as the molten material contracts, the well bottoms 20 are subjected to compression forces so that the bottoms 20 may become slightly bowed in a direction away from top rims 17 of wells 12. This curvature of bottoms 20 does not generally effect the utility of microplate 10 in a detrimental fashion. Moreover, the bowing of well bottoms 20 can actually assist in the reduction of the transmission of light or UV radiation between adjacent wells by distorting the path the light or UV radiation must take.

Figure 13:
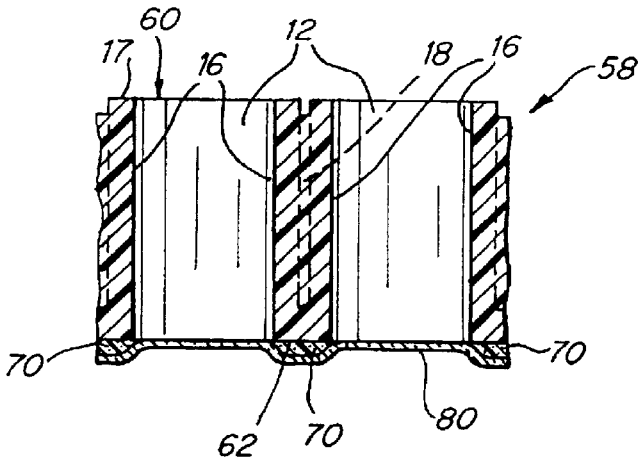
FIG. 13 is a partial cross-sectional view of an alternate embodiment of the microplate of the present invention.

FIG. 13 is a partial cross-sectional view of an alternate embodiment of the present invention in which a microplate 50 is manufactured by adhering an intermediate layer of material 70 to upper plate 60 and subsequently adhering a layer of UV permeable material 80 to the opposite side of intermediate layer 70. Upper plate 60 includes wells 12, top rims 17 and sidewalls 16 as describe above. In addition, although not shown in FIG. 13, upper plate 60 includes a frame 14. Upper plate 60 has a smooth surface 62 rather than ribs.

Upper plate 60 may be molded according to the procedures discussed above. However, a different mold piece is used that is similar to mold piece 40 (FIG. 6) without channels 56 so that upper plate 60 includes smooth surface 62.

Upper mold 60 and UV permeable layer 80 may be formed of materials that do not readily adhere to each other (e.g., a polyacrylic and Aclar® film). Therefore, to allow upper plate 60 and layer 80 to be incorporated into microplate 50, intermediate layer 70 is provided from a material that adheres to both upper plate 60 and UV permeable material 80. Layer 70 may be formed from a hot melt adhesive such as, for example, an ethylene vinyl acetate. In one embodiment, layer 70 is formed from Model 560 Thermo Plastic Bonding Film (3M, Minneapolis, Minn.).

Figure 14:
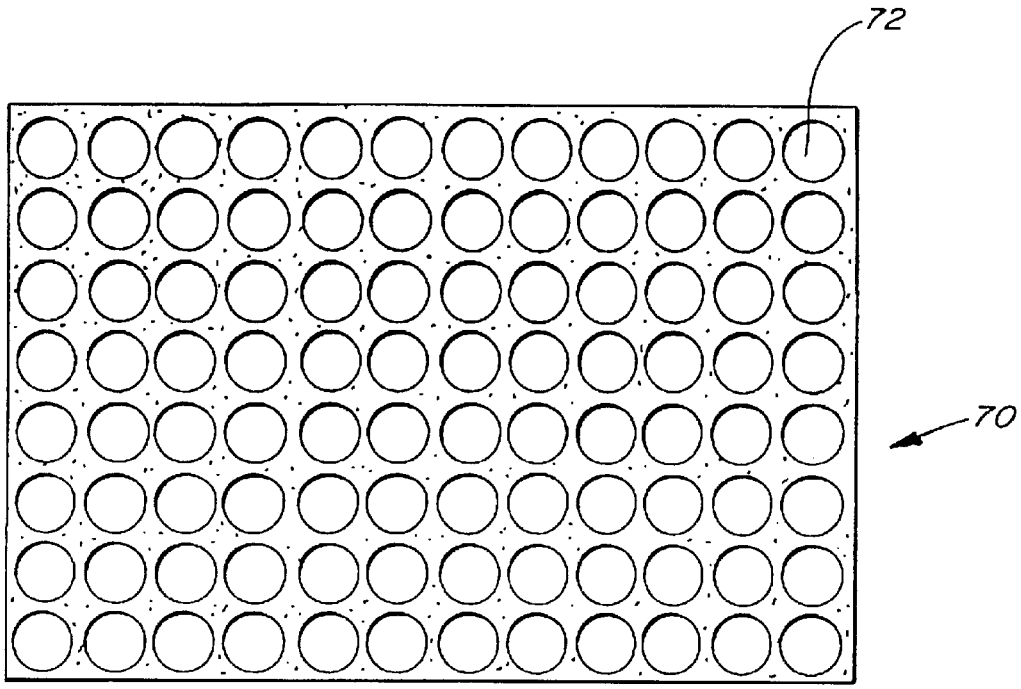
FIG. 14 is a top view of a layer of hot melt adhesive in accordance with one embodiment of the present invention.

Layer 70 may be formed from a UV impermeable material. For these embodiments, layer 70 should include holes 72 that are arranged so that, subsequent to the manufacture of microplate 50, holes 72 are aligned with the bottoms of wells 12 (FIGS. 13 and 14). Although shown in FIG. 14 as being circular in cross-section, holes 72 may have any cross-sectional design so long as layer 70 adheres to both upper plate 50 and layer 80 while not blocking the bottoms of wells 12.

The layer of UV permeable material 80 has the physical and chemical properties of sheet 24 discussed above. However, unlike sheet 24, material 80 need not include any holes passing therethrough because it need not accept the ribs.

When layer 70 is formed of a hot melt adhesive, the components of microplate 50 may be adhered using standard conditions and devices for hot melt adhesion. Typically, a pressure of from approximately 40 psig to approximately 80 psig is used at a temperature of from approximately 200° F. to approximately 300° F.

The following example is meant to be illustrative of one embodiment of the present invention and should not be construed as limiting.

EXAMPLE 1

A sheet formed of a corona-treated Aclar® film having a thickness of 7.5 mils and a molecular weight of greater than 10,000 (available from AlliedSignal, Inc., 101 Columbia Road, Morristown, N.J., 07692) was placed within a rib mold piece 40 having channels disposed therein. The rib mold piece was then fitted with a well-mold piece 38. Polystyrene (purchased from BASF, located in Mount Olive, N.J.) in a molten state was injected into the cavity through the injection gate 48 at a temperature of approximately 440° F. and a pressure of approximately 1200 psig. After filling the cavity with molten material, the pressure was reduced to 500 psig for approximately 6 seconds. The mold was allowed to partially cool by cooling the mold pieces to a temperature between approximately 95° F. and 120° F. with water. This injection/cooling process was repeated, and the mold was finally cooled and opened to remove the microplate.

Having thus described several illustrative embodiments of the present invention, various alterations, modifications and improvements may occur to those skilled in the art. Such alterations, modifications and improvements are intended to be within the spirit and scope of the invention. Accordingly, the foregoing description is by way of example only and is not limiting. The invention is limited only by the appended claims and their equivalents.

What is claimed is:

1. A microplate for use in assaying samples, comprising:

a frame that forms sidewalls of at least one well; and a first layer that forms a bottom of the at least one well, the first layer being formed from a plastic material having an average optical density that is no more than approximately 0.09 at a thickness of approximately 7.5 mils between wavelengths of approximately 200 nm and approximately 300 nm;

the bottom of the at least one wall having a thickness of less than approximately 14 mils.

2. The microplate according to claim 1, wherein the plastic material is a chlorotrifluoropolyethylene.

3. The microplate according to claim 1, wherein the bottom of the at least one well has a thickness of from approximately 2 mils to approximately 9 mils.

4. The microplate according to claim 1, wherein the frame and the first layer are molded together.

5. The microplate according to claim 1, wherein the frame is formed from a composite material including a filler and a base plastic material, the composite material having an optical density of no more than approximately 0.09 at a thickness of approximately 7.5 mils between wavelengths of approximately 200 nm and approximately 300 nm.

6. The microplate according to claim 1, wherein the frame is formed from a composite material including a filler and a base plastic material, the composite material having an average optical density of more than approximately 0.09 at a thickness of approximately 7.5 mils between wavelengths of approximately 200 nm and approximately 300 nm.

7. The microplate according to claim 1, farther comprising an intermediate layer disposed between the frame and the first layer.

8. The microplate according to claim 7, wherein the intermediate layer is formed from a hot melt adhesive.

9. The microplate according to claim 8, wherein the hot melt adhesive is an ethylene vinylacetate.

10. The microplate according to claim 7, wherein the intermediate layer includes a hole disposed above the bottom of the at least one well.

11. The microplate according to claim 1, wherein the at least one well includes first and second wells respectively having first and second bottoms, and wherein a difference between an average optical density of the first and second bottoms between wavelengths of approximately 200 nm and approximately 300 nm is no more than approximately 0.09.

12. A microplate for use in assaying samples, comprising:

a frame including an upper portion and a lower portion, the upper portion defining sidewalls of at least one well, the upper portion and the lower portion being contiguous; and a sheet defining a bottom of the at least one well, at least a portion of the sheet being disposed between the upper and lower portions of the frame;

the sheet having an average optical density that is no more than approximately 0.09 at a thickness of approximately 7.5 mils between wavelengths of approximately 200 nm and approximately 300 nm.

13. The microplate according to claim 12, wherein the upper and lower portions of the frame are a single molded piece.

14. The microplate according to claim 12, wherein the at least one well includes first and second wells, and wherein the lower portion includes a rib disposed between the first and second wells.

15. The microplate according to claim 12, wherein the at least one well includes a plurality of wells, and wherein the lower portion includes a grid of ribs, each of the ribs being disposed between adjacent ones of the plurality of wells.

16. The microplate according to claim 12, wherein the sheet has an outer edge, and wherein the lower portion of the frame includes at least one cleat disposed beneath at least a portion of the outer edge of the sheet.

17. The microplate according to claim 12, wherein the sheet has an outer edge, and wherein the lower portion of the frame includes a cleat disposed beneath the entire outer edge of the sheet.

18. The microplate according to claim 12, wherein the at least one well includes first and second wells respectively having first and second bottoms, and wherein a difference between an average optical density of the first and second bottoms between wavelengths of approximately 200 nm and approximately 300 nm is no more than approximately 0.09.

19. The microplate according to claim 12, wherein the bottom of the at least one well has a thickness of less than approximately 14 mils.

20. The microplate according to claim 12, wherein the bottom of the at least one well has a thickness of from approximately 2 mils to approximately 9 mils.

21. The microplate according to claim 12, wherein the sheet is formed from a polychlorotrifluoroethylene.

22. The microplate according to claim 12, wherein the frame and the sheet are molded together.

23. The microplate according to claim 12, wherein the frame is formed from a composite material including a filler and a base plastic material, the composite material having an optical density of no more than approximately 0.09 at a thickness of approximately 7.5 mils between wavelengths of approximately 200 nm and approximately 300 nm.

24. The microplate according to claim 12, wherein the frame is formed from a composite material including a filler and a base plastic material, the composite material having an average optical density of more than approximately 0.09 at a thickness of approximately 7.5 mils between wavelengths of approximately 200 nm and approximately 300 nm.

*25. A microplate for use in assaying samples, comprising:*

*a frame that forms sidewalls of at least one well; and*

*a first layer that forms a bottom of the at least one well, the first layer being formed from a plastic material having an average optical density that is no more than approximately 0.09 at a thickness of approximately 7.5 mils between wavelengths of approximately 260 nm and approximately 280 nm;*

*the bottom of the at least one well having a thickness of less than approximately 14 mils.*

*26. A microplate for use in assaying samples, comprising:*

*a frame that forms sidewalls of at least one well; and*

*a first layer that forms a bottom of the at least one well, the first layer being formed from a plastic material having an optical density that is no more than approximately 0.09 at a thickness of approximately 7.5 mils at a wavelength of 280 nm;*

*the bottom of the at least one well having a thickness of less than approximately 14 mils.*

*27. A microplate for use in assaying samples, comprising:*

*a frame that forms sidewalls of at least one well; and*

*a first layer that forms a bottom of the at least one well, the first layer being formed from a plastic material that allows greater than approximately 80% radiation transmission therethrough at a thickness of approximately 7.5 mils at a wavelength of 280 nm;*

*the bottom of the at least one well having a thickness of less than approximately 14 mils.*

* * * * *